(12) United States Patent
Yamauchi et al.

(10) Patent No.: US 7,168,295 B2
(45) Date of Patent: Jan. 30, 2007

(54) GAS SENSOR

(75) Inventors: Masanobu Yamauchi, Kariya (JP); Motoaki Satou, Anjo (JP); Kiyomi Kobayashi, Kuwana (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 11/090,010

(22) Filed: Mar. 28, 2005

(65) Prior Publication Data
US 2005/0241368 A1 Nov. 3, 2005

(30) Foreign Application Priority Data
Apr. 13, 2004 (JP) .............................. 2004-118160
Feb. 3, 2005 (JP) .............................. 2005-027438

(51) Int. Cl.
*G01N 27/407* (2006.01)
*G01N 37/00* (2006.01)

(52) U.S. Cl. .................... 73/31.05; 73/23.31; 204/424; 204/431

(58) Field of Classification Search ................ 73/23.2, 73/23.31, 31.05; 204/424, 431
See application file for complete search history.

(56) References Cited

U.S. PATENT DOCUMENTS

| | | | |
|---|---|---|---|
| 5,039,972 A * | 8/1991 | Kato et al. ..................... 338/34 |
| 5,846,391 A | 12/1998 | Friese et al. ................. 204/424 |
| 6,418,777 B1 * | 7/2002 | Noda et al. ................... 73/23.2 |
| 6,510,728 B2 | 1/2003 | Matsuo et al. |
| 2001/0023611 A1 | 9/2001 | Matsuo et al. |
| 2003/0116435 A1 * | 6/2003 | Satou et al. ................. 204/424 |

FOREIGN PATENT DOCUMENTS

| | | |
|---|---|---|
| JP | 10-508384 | 8/1998 |
| JP | 2001-281209 | 10/2001 |

* cited by examiner

*Primary Examiner*—Daniel S. Larkin
(74) *Attorney, Agent, or Firm*—Nixon & Vanderhye PC

(57) ABSTRACT

A gas sensor has a sensor element inserted in a cylindrical housing. A measured gas cover, provided at a distal end side of the housing, forms a measured gas environment at a distal end side of the sensor element. An atmospheric air cover, provided at a proximal end side of the housing, forms an atmospheric air environment at a proximal end side of the sensor element. A clearance between an inside surface of the housing and an outside surface of the sensor element is gastightly sealed with a sealing member including a plurality of powder filler layers to separate or isolate the measured gas environment from the atmospheric air environment.

27 Claims, 10 Drawing Sheets

GAS SENSOR

CROSS-REFERENCE TO RELATED APPLICATION

This application is based upon and claims the benefit of priority from earlier Japanese Patent Application No. 2004-118160 filed on Apr. 13, 2004 and the Japanese Patent Application No. 2005-27438 filed on Feb. 3, 2005 so that the descriptions of which are incorporated herein by reference.

BACKGROUND OF THE INVENTION

The present invention relates to a gas sensor installed in an exhaust system of an internal combustion engine for an automotive vehicle to control the air-fuel ratio of fuel mixture supplied into a combination chamber of the engine.

FIG. 12 shows a conventional gas sensor 9 installed in an exhaust system of an automotive engine to control the air-fuel ratio of fuel mixture. The gas sensor 9 includes a sensor element 1002 inserted in a cylindrical housing 1010, a measured gas cover 1011 provided at a distal end side of the housing 1010 to cover a distal end side of the sensor element 1002, and an atmospheric air cover 1012 provided at a proximal end side of the housing 1010 to cover a proximal end side of the sensor element 1002.

According to this conventional gas sensor 9, the inside space of the measured gas cover 1011 is a measured gas environment 1110, while the inside space of the atmospheric air cover 1012 is an atmospheric air environment 1120. The clearance between the sensor element 1002 and the housing 1010 should be gastightly sealed, to separate or isolate these environments 1110 and 1120 from each other. Furthermore, the clearance between the sensor element 1002 and the housing 1010 should be watertightly sealed. Watertightly sealing the clearance between the sensor element 1002 and the housing 1010 brings the effect of preventing fuel liquid from entering from the measured gas environment 1110 during the engine startup operation and also brings the effect of preventing condensate from entering from the measured gas environment 1110 during the engine stopped condition.

Regarding a seal arrangement between the sensor element 1002 and the housing 1010, the U.S. Pat. No. 6,510,728 discloses a method of using inorganic powders or a molded product of inorganic powders. More specifically, as shown in FIG. 12, the inorganic powders are filled into the clearance between the sensor element 1002 and the housing 1010. And then, the inorganic powders are pressed to form a powder filler 1091. Subsequently, an insulator 1192 and a metallic ring 1193 are disposed on the powder filler 1091. Alternatively, it is possible to manufacture a temporary molded article beforehand by temporarily molding inorganic powders into a shape substantially identical with a space formed between the sensor element 1002 and the housing 1010. The temporary molded article is disposed in this space, and then pressed to fill and provide a gastight and watertight sealing between the sensor element 1002 and the housing 1010.

The measured gas cover 1011 consists of an outer cover 1111 and an inner cover 1112. The atmospheric air cover 1012 consists of a main cover member 1121 and an outside cover member 1122. Furthermore, an atmospheric air side insulator 1013 holds lead wires 1015 of the sensor element 1002. The lead wires 1015 are inserted in an elastic insulating member 1016 provided at the proximal end side of the atmospheric air side insulator 1013.

In general, there is the tendency that recent advanced engines discharge high-temperature exhaust gases. It is therefore required that a seal arrangement between the sensor element and the housing possesses excellent high-temperature durability. According to a conventional sealing method, an appropriate amount of additive agent is mixed with inorganic powders to increase the density of pressed inorganic powders and enhance the sealing properties. However, conventionally known additive agents tend to decompose at high temperatures. Therefore, the conventional known additive agents cannot be used for the gas sensors which are subjected to high-temperature environments.

If a gas sensor uses inorganic powder filler containing no additive agents, sealing properties (e.g. gastightness and watertightness) of this sensor will soon deteriorate in accordance with cumulative time of engine operations even if good sealing properties are assured in a brand-new condition of this sensor. To enhance the sealing properties, it may be possible to use a higher pressure in the process of pressing inorganic powders so as to increase the density of the inorganic powder filler. However, applying a higher pressure to inorganic powders may lead to generation of cracks in the sensor element because the sensor element is a fragile ceramic product which is weak against shock.

Furthermore, as disclosed in the U.S. Pat. No. 5,846,391, it is conventionally proposed to use a powder filler arrangement consisting of three layers of steatite, boron nitride, and steatite to increase the sealing properties. However, a hot press forming operation performed at high temperatures of approximately 2000° C. is required to form the boron nitride layer, although steatite layers can be formed through the sintering operations performed at low temperatures of approximately 500° C. In other words, to realize the hot press forming operation, this prior art technique requires a special furnace having sufficient high-temperature durability. This will increase the thermal energy cost.

In view of the foregoing, it is required to provide an excellent seal arrangement between the sensor element and the housing of a gas sensor, which is capable of assuring excellent sealing properties and accordingly capable of maintaining long-lasting watertightness and gastightness, and requires no special apparatus in the manufacturing processes and accordingly realizes easy manufacturing method.

Meanwhile, there is a conventional gas sensor including an element assembly, consisting of a sensor element and a surrounding cylindrical insulating tube, which is inserted in a cylindrical housing. A measured gas cover is provided at a distal end side of the housing to cover a distal end side of the sensor element. And, an atmospheric air cover is provided at a proximal end side of the housing to cover a proximal end side of the sensor element. The gas sensor having such an arrangement is not free from the above-described problems, as well. Thus, it is required to provide an excellent seal arrangement assuring long-lasting sealing properties (i.e. watertightness and gastightness) between the element assembly and the housing of a gas sensor, which requires no special apparatus in the manufacturing processes and accordingly realizes easy manufacturing method.

SUMMARY OF THE INVENTION

In view of the above-described problems, the present invention has an object to provide a gas sensor having a sealing arrangement assuring excellent sealing properties and also has an object to provide a related manufacturing method.

In order to accomplish the above and other related objects, the present invention provides a gas sensor including a sensor element (or an element assembly of the sensor element and a surrounding cylindrical insulating tube) inserted in a cylindrical housing, a measured gas cover provided at a distal end side of the housing to cover a distal end side of the sensor element, and an atmospheric air cover provided at a proximal end side of the housing to cover a proximal end side of the sensor element. According to the gas sensor of the present invention, a clearance between an inside surface of the housing and an outside surface of the sensor element (or the element assembly) is gastightly sealed with a sealing member including a plurality of powder filler layers.

Furthermore, the present invention provides a method for manufacturing the above-described gas sensor including the steps of inserting the sensor element (or the element assembly) in the housing, disposing one temporary molded article between the housing and the sensor element (or the element assembly), pressing and filling the temporary molded article from above to form a single powder filler layer, and repeating the above disposing and pressing/filling processes to form the plurality of powder filler layers of the sealing member.

Furthermore, the present invention provides another method for manufacturing the above-described gas sensor including the steps of inserting the sensor element (or the element assembly) in the housing, disposing plural temporary molded articles between the housing and the sensor element (or the element assembly), and simultaneously pressing and filling all of the plural temporary molded articles from above to form the plurality of powder filler layers of the sealing member.

Furthermore, the present invention provides yet another method for manufacturing the above-described gas sensor including the steps of inserting the sensor element (or the element assembly) in the housing, filling predetermined powder material between the housing and the sensor element (or the element assembly), pressing the predetermined powder material from above to form a single powder filler layer, and repeating the above filling and pressing processes to form the plurality of powder filler layers of the sealing member.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
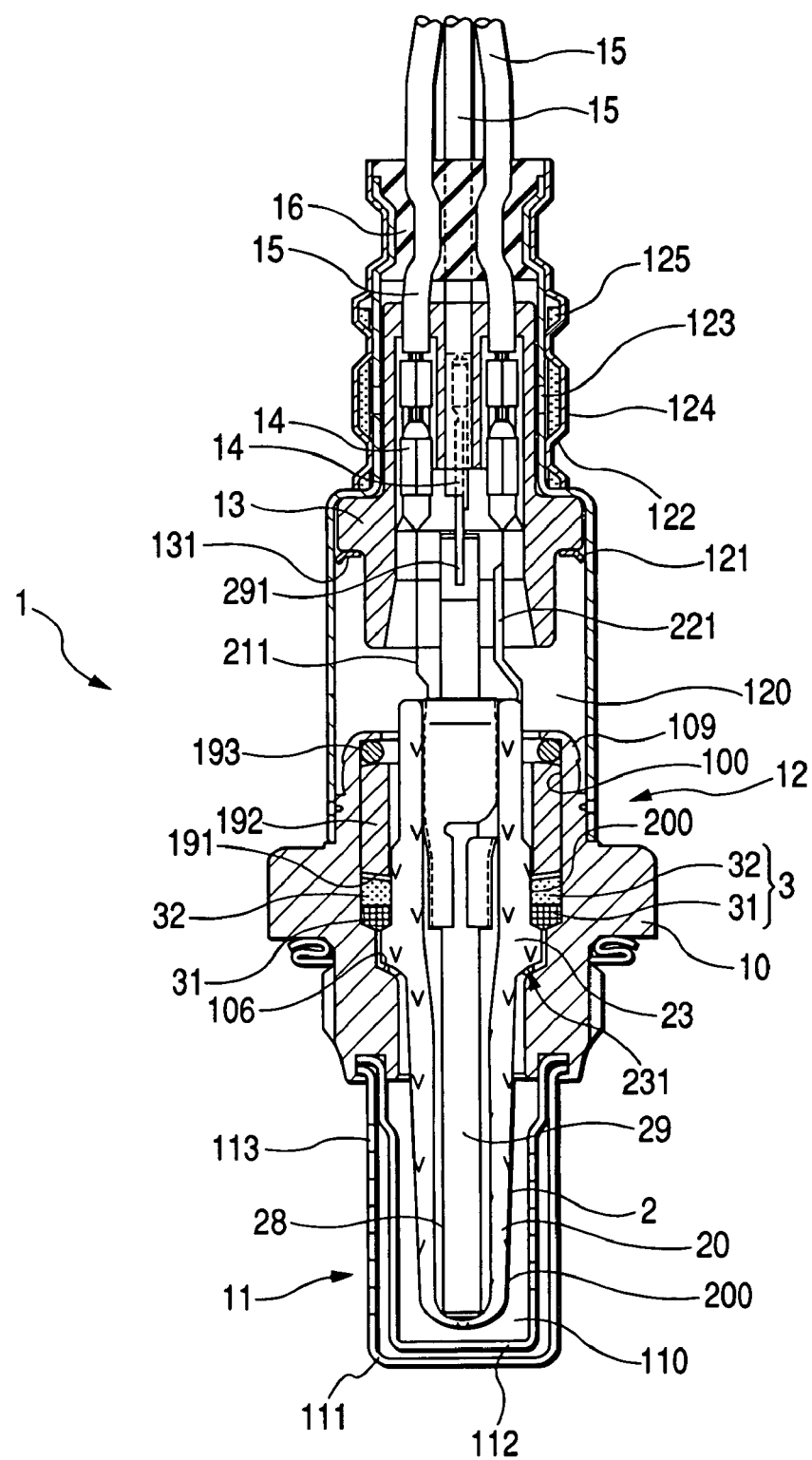
FIG. 1 is a vertical cross-sectional view showing an overall arrangement of a gas sensor in accordance with a first embodiment of the present invention.

As preferable modes for embodying the present invention, this application discloses two gas sensors and related manufacturing methods.

More specifically, the present invention provides a first gas sensor including a sensor element inserted in a cylindrical housing, a measured gas cover provided at a distal end side of the housing to cover a distal end side of the sensor element, and an atmospheric air cover provided at a proximal end side of the housing to cover a proximal end side of the sensor element. According to the first gas sensor, a clearance between an inside surface of the housing and an outside surface of the sensor element is gastightly sealed with a sealing member including a plurality of powder filler layers.

Furthermore, the present invention provides a second gas sensor including an element assembly inserted in a cylindrical housing. This element assembly includes a sensor element and a cylindrical insulating tube assembled around the sensor element. The second gas sensor of the present invention further includes a measured gas cover provided at a distal end side of the housing to cover a distal end side of the sensor element, and an atmospheric air cover provided at a proximal end side of the housing to cover a proximal end side of the sensor element. According to the second gas sensor, a clearance between an inside surface of the housing and an outside surface of the element assembly is gastightly sealed with a sealing member including a plurality of powder filler layers.

The first gas sensor of the present invention has the sealing member including a plurality of powder filler layers provided to seal the clearance between the sensor element and the housing. The second gas sensor of the present invention has the sealing member including a plurality of powder filler layers provided to seal the clearance between the element assembly and the housing. Providing plural powder filler layers enhances the sealing properties and accordingly brings the effect of surely separating or isolating the measured gas environment formed inside the measured gas cover from the atmospheric air environment formed inside the atmospheric air cover. The watertightness can be improved, and accordingly it becomes possible to surely eliminate immersion of the liquid entering from the measured gas environment. Furthermore, the density of the sealing member becomes uniform and high. The density does not vary so easily and accordingly it becomes possible to maintain long-lasting and excellent sealing properties.

The present invention provides a first method for manufacturing a gas sensor including a sensor element inserted in a cylindrical housing, a measured gas cover provided at a distal end side of the housing to cover a distal end side of the sensor element, and an atmospheric air cover provided at a proximal end side of the housing to cover a proximal end side of the sensor element. The first manufacturing method of the present invention includes first to third steps. In the first step, the sensor element is inserted in the housing. In the second step, one temporary molded article is disposed between the housing and the sensor element. This temporary molded article is manufactured by temporarily molding predetermined powder material. In the third step performed after accomplishing the second step, the temporary molded article is pressed and filled from above to form a single powder filler layer. Furthermore, according to the first manufacturing method of the present invention, the above second and third steps are repeated to form a plurality of powder filler layers of a sealing member, thereby gastightly sealing a clearance between an inside surface of the housing and an outside surface of the sensor element with the sealing member including the plurality of powder filler layers.

The present invention provides a second method for manufacturing a gas sensor including a sensor element inserted in a cylindrical housing, a measured gas cover provided at a distal end side of the housing to cover a distal end side of the sensor element, and an atmospheric air cover provided at a proximal end side of the housing to cover a proximal end side of the sensor element. The second manufacturing method of the present invention includes first to third steps. In the first step, the sensor element is inserted in the housing. In the second step, plural temporary molded articles are disposed between the housing and the sensor element. Each of the temporary molded articles is manufactured by temporarily molding predetermined powder material. In a third step, all of the plural temporary molded articles are simultaneously pressed and filled from above to form a plurality of powder filler layers of a sealing member, thereby gastightly sealing a clearance between an inside surface of the housing and an outside surface of the sensor element with the sealing member including the plurality of powder filler layers.

The present invention provides a third method for manufacturing a gas sensor including an element assembly of a sensor element and a surrounding cylindrical insulating tube which are integrally inserted in a cylindrical housing, a measured gas cover provided at a distal end side of the housing to cover a distal end side of the sensor element, and an atmospheric air cover provided at a proximal end side of the housing to cover a proximal end side of the sensor element. The third manufacturing method of the present invention includes first to third steps. In the first step, the element assembly is inserted in the housing. In the second step, one temporary molded article is disposed between the housing and the element assembly. This temporary molded article is manufactured by temporarily molding predetermined powder material. In the third step performed after accomplishing the second step, the temporary molded article is pressed and filled from above to form a single powder filler layer. Furthermore, according to the third manufacturing method of the present invention, the second and third steps are repeated to form a plurality of powder filler layers of a sealing member, thereby gastightly sealing a clearance between an inside surface of the housing and an outside surface of the element assembly with the sealing member including the plurality of powder filler layers.

The present invention provides a fourth method for manufacturing a gas sensor including an element assembly of a sensor element and a surrounding cylindrical insulating tube which are integrally inserted in a cylindrical housing, a measured gas cover provided at a distal end side of the housing to cover a distal end side of the sensor element, and an atmospheric air cover provided at a proximal end side of the housing to cover a proximal end side of the sensor element. The fourth manufacturing method of the present invention includes first to third steps. In the first step, the element assembly is inserted in the housing. In the second step, plural temporary molded articles are disposed between the housing and the element assembly. Each of the temporary molded articles is manufactured by temporarily molding predetermined powder material. In the third step performed after accomplishing the second step, all of the plural temporary molded articles are simultaneously pressed and filled from above to form a plurality of powder filler layers of a sealing member, thereby gastightly sealing a clearance between an inside surface of the housing and an outside surface of the element assembly with the sealing member including the plurality of powder filler layers.

According to the above manufacturing methods of the present invention, the temporary molded articles of powder materials are prepared beforehand for respective powder filler layers and then disposed and pressed to provide a gastight seal arrangement between the sensor element and the housing (first and second manufacturing methods), or between the element assembly and the housing (third and fourth manufacturing methods). According to the first and third manufacturing methods of the present invention, each temporary molded article of powder material is disposed and then pressed to obtain a single powder filler layer, and these steps are repeated to successively obtain the plural powder filler layers. According to the second and fourth manufacturing methods of the present invention, plural temporary molded articles of powder materials are disposed and pressed together to simultaneously obtain the plural powder filler layers.

The gas sensor, manufactured according to any one of the first to fourth manufacturing methods of the present invention, has the sealing member including a plurality of powder filler layers. The sealing properties of the gas sensor can be enhanced. Thus, it becomes possible to surely separate or isolate the measured gas environment formed inside the measured gas cover from the atmospheric air environment formed inside the atmospheric air cover. The watertightness can be improved, and accordingly it becomes possible to surely eliminate immersion of the liquid entering from the measured gas environment. Furthermore, the density of the sealing member becomes uniform and high. The density does not vary so easily and accordingly it becomes possible to maintain long-lasting and excellent sealing properties. Furthermore, the first to fourth manufacturing methods of the present invention require no special powder materials. Furthermore, the sealing member can be manufactured by using a simple manufacturing method including a step of temporarily molding the powder material and a step of pressing the temporary molded article. Thus, no special apparatus is required to manufacture the sealing member, and accordingly the sealing member can be easily manufactured.

Meanwhile, the present invention provides a fifth method for manufacturing a gas sensor including a sensor element inserted in a cylindrical housing, a measured gas cover provided at a distal end side of the housing to cover a distal end side of the sensor element, and an atmospheric air cover provided at a proximal end side of the housing to cover a proximal end side of the sensor element. The fifth manufacturing method of the present invention includes first to third steps. In the first step, the sensor element is inserted in the housing. In the second step, predetermined powder material is filled between the housing and the sensor element. And, in the third step performed after accomplishing the second step, the predetermined powder material is pressed from above to form a single powder filler layer. Furthermore, according to the fifth manufacturing method of the present invention, the second and third steps are repeated to form a plurality of powder filler layers of a sealing member, thereby gastightly sealing a clearance between an inside surface of the housing and an outside surface of the sensor element with the sealing member including the plurality of powder filler layers.

Moreover, the present invention provides a sixth method for manufacturing a gas sensor including an element assembly of a sensor element and a surrounding cylindrical insulating tube which are integrally inserted in a cylindrical housing, a measured gas cover provided at a distal end side of the housing to cover a distal end side of the sensor element, and an atmospheric air cover provided at a proximal end side of the housing to cover a proximal end side of the sensor element. The sixth manufacturing method of the present invention includes first to third steps. In the first step, the element assembly is inserted in the housing. In the second step, predetermined powder material is filled between the housing and the element assembly. And, in the third step performed after accomplishing the second step, the predetermined powder material is pressed from above to form a single powder filler layer. Furthermore, according to the sixth manufacturing method of the present invention, the second and third steps are repeated to form a plurality of powder filler layers of a sealing member, thereby gastightly sealing a clearance between an inside surface of the housing and an outside surface of the element assembly with the sealing member including the plurality of powder filler layers.

According to the fifth and sixth manufacturing methods of the present invention, the powder materials are directly filled and pressed to obtain powder filler layers between the sensor element and the housing (fifth manufacturing method), or between the element assembly and the housing (sixth manufacturing method). The gas sensor, manufactured according to the fifth or sixth manufacturing method of the present invention, has the sealing member including a plurality of powder filler layers. The sealing properties of the gas sensor can be enhanced. Thus, it becomes possible to surely separate or isolate the measured gas environment formed inside the measured gas cover from the atmospheric air environment formed inside the atmospheric air cover. The watertightness can be improved, and accordingly it becomes possible to surely eliminate immersion of the liquid entering from the measured gas environment. Furthermore, the density of the sealing member becomes uniform and high. The density does not vary so easily and accordingly it becomes possible to maintain long-lasting and excellent sealing properties. Furthermore, the fifth and sixth manufacturing methods of the present invention require no special powder materials. Furthermore, the sealing member can be manufactured by using a simple manufacturing method including a step of temporarily molding the powder material and a step of pressing the temporary molded article. Thus, no special apparatus is required to manufacture the sealing member, and accordingly the sealing member can be easily manufactured.

As described above, the present invention provides an excellent seal arrangement assuring long-lasting sealing properties (i.e. watertightness and gastightness) between the element assembly and the housing of a gas sensor, which requires no special apparatus in the manufacturing processes and accordingly realizes easy manufacturing method.

The gas sensor of the present invention has a cup-shaped sensor element or a multilayered sensor element. Furthermore, the present invention is applicable to a gas sensor including a sensor element assembled in a housing (refer to a later-described first embodiment and FIG. 1), or a gas sensor including a sensor element assembled together with a surrounding insulating tube to form an element assembly which is disposed in a housing (refer to a later-described fourth embodiment and FIG. 10). Furthermore, the present invention is applicable to a gas sensor measuring the oxygen concentration in a measured gas, or a gas sensor measuring the gas concentration, such as NOx concentration, HC concentration, CO concentration, other than the oxygen concentration. Furthermore, the present invention is applicable to a gas sensor installed in an exhaust system of an internal combustion engine for an automotive vehicle to measure the air-fuel ratio of fuel mixture introduced into a combustion chamber of this engine and control the combustion of fuel mixture based on the measured air-fuel ratio.

According to the present invention, it is possible to arrange each of the plural powder filler layers by using powder materials being mutually differentiated in particle size and/or composition. Alternatively, it is possible to form each of the plural powder filler layers by using powder materials having the same particle size and/or composition. Furthermore, it is possible to arrange each of the plural powder filler layers by using powders having uniform or substantially the same particle size, or by using powders somewhat differentiated in their particle sizes. In the case that the same powder material is used to arrange a plurality of powder filler layers, it may be difficult to discriminate the boundaries between respective filler layers, although the effects of the present invention will be obtained.

According to the first or second gas sensor of the present invention, it is preferable that the plural powder filler layers include predetermined powder material containing particles whose particle sizes are in a range from 80 to 1000 μm by an amount equal to or greater than 80 wt. % of the entire weight. This arrangement can increase the density of each powder filler layer and accordingly can realize a highly densified sealing member. If the particles having particle sizes less than 80 μm exceeds 80 wt. % of the entire weight, there will be the possibility that many micro particles exist between contact surfaces of the particles arranging the powder material. Accordingly, the density (i.e. adherence between particles) will deteriorate and also the watertightness will deteriorate. If the particles having particle sizes exceeding 1000 μm exceeds 80 wt. % of the entire weight, respective particles will not sufficiently deform when the pressure is applied in the process of manufacturing the powder filler layer. Thus, the filling properties will be worsened and therefore it will be difficult to obtain excellent gastightness.

According to the first or second gas sensor of the present invention, it is preferable that the plurality of powder filler layers include a first powder filler layer positioned closest to the distal end side of the gas sensor. The first powder filler layer contacts with an inside inclined surface provided on an outside surface of the sensor element or the element assembly and inclined from the sensor element to the housing. The first powder filler layer contacts with an outside inclined surface provided on an inside surface of the housing and inclined from the housing to the sensor element. Furthermore, conditions of $0° \leq C \leq 50°$, $0° \leq D \leq 50°$, and $120° \leq E \leq 180°$ are satisfied. In this case, 'C' represents an angle formed between the inside inclined surface and a line normal to an axial direction of the gas sensor, 'D' represents an angle formed between the outside inclined surface and a line normal to the axial direction of the gas sensor, and 'E' represents an angle formed between the inside inclined surface and the outside inclined surface.

According to this arrangement, it becomes possible to assure excellent gastightness and watertightness. If the angle C is greater than 50° and/or the angle D is greater than 50°, the density of the lower part of the first powder filler layer (i.e. the distal end side of the gas sensor) will not increase sufficiently and accordingly gastightness and watertightness will deteriorate. Furthermore, there is the possibility that a significant amount of permanent set in fatigue will appear when it is used for a long time. Furthermore, if the angle E is less than 120° or greater than 180°, the density of the lower part of the first powder filler layer (i.e. the distal end side of the gas sensor) will not increase sufficiently and accordingly gastightness and watertightness will deteriorate. Furthermore, there is the possibility that a significant amount of permanent set in fatigue will appear when it is used for a long time.

According to the first or second gas sensor of the present invention, it is preferable that the gas sensor further includes a packing member contacting with an end surface of at least one of the plurality powder filler layers. According to this arrangement, the packing member can prevent the powder filler from undesirably leaking into its surrounding clearance. In the process of manufacturing the powder filler layers, the packing member prevents the powder filler from adhering on the pressing die and accordingly it becomes possible to maintain excellent sealing properties.

According to a gas sensor of a later-described first embodiment of the present invention, the above-described surrounding clearance is, for example, a clearance between the housing and the sensor element, a clearance between these members and the pressing die (i.e. a member 41 shown in FIG. 4), a clearance between the powder filler layers and the housing or the sensor element, or a clearance between an insulator (i.e. a member 192 shown in FIG. 1) provided above the powder filler layers and the housing or the sensor element.

Furthermore, regarding an example using a packing, as shown in FIG. 1 of the later-described first embodiment, it is possible to laminate the second powder filler layer on the first powder filler layer and dispose the packing member on the second powder filler layer. Furthermore, although not shown in the drawing, in a clearance between the sensor element and the housing, it is possible to provide the packing member beneath the powder filler layer positioned at the distal end side. Furthermore, it is possible to provide a plurality of packing members on the upper surfaces of respective powder filler layers. In practice, it is possible to use a vermiculite molded product or a ceramic fiber molded product as the packing member of this invention.

According to the first or second gas sensor of the present invention, it is preferable that at least one of plural powder filler layers contains auxiliary filler. The auxiliary filler has the function of filling the clearance between the contact surfaces of neighboring particles of the powder material arranging the powder filler layer. Thus, the auxiliary filler can improve the adherence between particles and accordingly can highly densify the powder filler layer. Thus, it becomes possible to obtain excellent sealing properties. Furthermore, in the case that the clearances of neighboring particles in the powder filler layer are filled with the auxiliary filler, the liquid will not enter into the clearance due to the capillary action.

Regarding the auxiliary filler of the present invention, it is preferable that the auxiliary filler is selected from the group consisting of an aqueous solution of primary aluminum phosphate, an aqueous solution of sodium silicate, and an aqueous solution of potassium silicate. These aqueous solutions can efficiently enter into narrow clearances of neighboring particles in the powder material arranging the powder filler layer. Thus, these aqueous solutions can increase the density of powder filler layers and accordingly can assure excellent sealing properties.

Furthermore, when the auxiliary filler is selected from the group consisting of an aqueous solution of primary aluminum phosphate, an aqueous solution of sodium silicate, and an aqueous solution of potassium silicate, it is preferable that the content of the auxiliary filler is in a range from 0.1 to 10 wt. % relative to 100 wt. % of at least one of the plurality of powder filler layers. According to this arrangement, it becomes possible to obtain a highly densified powder filler layer. If the content of the auxiliary filler is less than 0.1 wt. %, clearances of neighboring particles in the powder material arranging the powder filler layer will not be sufficiently filled with the auxiliary filler and accordingly it will be difficult to obtain highly densified powder filler. On the other hand, if the content of the auxiliary filler is greater than 10 wt. %, the amount of the auxiliary filler will be so excessive that the filling properties of the particles will be rather worsened and the powder filler layer cannot possess sufficient specific gravity. Thus, the sealing properties of the powder filler layer will deteriorate.

Furthermore, it is preferable that the auxiliary filler contains at least one component selected from the group consisting of barium hydroxide, borosilicate glass, alumino-silicate glass, soda-lime silicate glass, lead silicate glass, low-melting borate glass, lime alumino-based glass, and aluminate glass. These materials can be liquefied at relatively low temperatures. Therefore, even if a heat treatment is applied to the auxiliary filler to obtain liquefied auxiliary filler and eliminate clearances of the particles in the powder filler layers with the liquefied auxiliary filler, such a heat treatment will be done at relatively low temperatures without giving adverse thermal influences to the housing, the gas sensor element, and other components arranging the gas sensor. Furthermore, these materials can smoothly enter, in liquefied state, into narrow clearances of the particles arranging the powder filler layers, and accordingly can close permeation passages formed in the powder filler layers. Thus, it becomes possible to eliminate immersion of gasoline or any other liquid components contained in the exhaust gas which may undesirably enter via the permeation passages formed in the powder filler layers. Accordingly, it becomes possible to obtain excellent sealing properties.

Furthermore, when the auxiliary filler contains at least one component selected from the group consisting of barium hydroxide, borosilicate glass, alumino-silicate glass, soda-lime silicate glass, lead silicate glass, low-melting borate glass, lime alumino-based glass, and aluminate glass, it is preferable that the content of the auxiliary filler is in a range from 0.5 to 30 wt. % relative to 100 wt. % of at least one of the plurality of powder filler layers. According to this arrangement, it becomes possible to obtain a highly densified powder filler layer. If the content of the auxiliary filler is less than 0.5 wt. %, the clearances of neighboring particles in the powder material arranging the powder filler layer will not be sufficiently filled with the auxiliary filler and accordingly it will be difficult to obtain highly densified powder filler. On the other hand, if the content of the auxiliary filler is greater than 30 wt. %, the amount of the auxiliary filler will be so excessive that the filling properties of the particles will be rather worsened and the powder filler layer cannot possess sufficient specific gravity. Thus, the sealing properties of the powder filler layer will deteriorate.

According to the first or second gas sensor of the present invention, it is preferable that the powder filler layers contain either talc or boron nitride by an amount equal to or greater than 50 wt. % relative to 100 wt. % of the powder filler layers. As the molding of talc can be done at room temperatures, thermal energy can be saved. Furthermore, the talc particles are scaly particles having a layered structure. When the talc particles are pressed, they cause cleavage in the layered direction while maintaining the layered structure of the scaly particles. Furthermore, as the talc particles are sufficiently soft (Mohs hardness=1), the scaly particles can deform so as to eliminate the clearances remaining between the talc particles before obtaining the powder filler layers. Therefore, the specific gravity can be increased and accordingly excellent sealing properties can be easily obtained. As is well known, talc is comprised of clay minerals and is a natural material containing MgO and $SiO_2$ as the main components.

Furthermore, as the boron nitride particles are sufficiently soft, these particles can deform so as to eliminate the clearances remaining between the boron nitride particles before obtaining the powder filler layers. Therefore, the specific gravity can be increased and accordingly excellent sealing properties can be easily obtained.

Furthermore, if the content of talc or boron nitride is less than 50 wt. %, their particles will not be able to deform so as to sufficiently eliminate tiny clearances. It will be possible to obtain ideal powder filler layers if the content of talc and/or boron nitride is 100 wt. %. In other words, it will be ideal that the powder filler layers consist of boron nitride only or consist of a combination of talc and boron nitride.

According to the first or sixth manufacturing method for a gas sensor of the present invention, in providing the sealing member including a plurality of powder filler layers, it is possible to use temporary molded articles which are temporarily molded beforehand or use the powder materials directly. When a plurality of powder filler layers are formed in a single gas sensor, it is possible to form respective layers by using powder materials or by using temporary molded articles which are temporarily molded beforehand. As shown in a first embodiment of the present invention, it is preferable that the temporary molded articles have simple cylindrical shapes and are later pressed and deformed into the shapes corresponding to the space formed between the sensor element (or the element assembly) and the housing. Alternatively, it is possible to prepare temporary molded articles being configured beforehand so as to correspond to the space formed between the sensor element (or the element assembly) and the housing. In this case, it is preferable to press the temporary molded articles to increase their densities before obtaining the powder filler layers.

According to the first or fourth manufacturing method for a gas sensor of the present invention, it is preferable that the temporary molded article is manufactured by disposing layers of different powder materials. More specifically, although one temporary molded article forms one powder filler layer, a single powder filler layer can be formed by using a temporary molded article which includes a plurality of layers of powder materials containing particles differentiated in composition and/or in particle size. The effects of the present invention can be obtained similarly.

According to the first or fourth manufacturing method for a gas sensor of the present invention, it is preferable that a relationship $1.0 \leq B/A \leq 5$ is satisfied where 'A' represents a maximum width of the sealing member including the plurality of powder filler layers, as a length measured along a radial direction of the gas sensor, and 'B' represents a maximum thickness of the sealing member including the plurality of powder filler layers, as a length measured along an axial direction of the gas sensor. This setting can greatly enhance gastightness and/or watertightness (refer to the second embodiment). If the value B/A is less than 1.0 or greater than 5, there will be the possibility that gastightness or watertightness may deterirate.

Furthermore, it is preferable that the temporary molded article is manufactured by disposing an odd number of plural layers of different powder materials so as to form a symmetrical laminated structure. In this case, the temporary molded article can be obtained as a symmetrical product having the same configuration at its distal end side and its proximal end side. Therefore, in the assembling process of the temporary molded article to be disposed between the housing and the sensor element or between the housing and the element assembly, it is unnecessary to carefully check the correct direction of the temporary molded article. Thus, it becomes possible to improve the efficiency in the assembling work, and accordingly the productivity of the gas sensor can be improved.

According to the first or second gas sensor of the present invention, it is preferable that a powder filler layer disposed closest to the distal end side of the sealing member contains the auxiliary filler. In this case, the dense powder filler layer can be disposed at the distal end side, i.e. at the position closest to the measured gas environment. Accordingly, it becomes possible to surely eliminate immersion of the liquid entering from the measured gas environment.

Furthermore, it is preferable that the sealing member includes another powder filler layer containing no auxiliary filler. In this case, it becomes possible to assure excellent watertightness and gastightness at high temperatures. More specifically, excellent watertightness will be secured when the powder filler layer containing the auxiliary filler is disposed at the distal end side. However, it may be difficult to sufficiently secure excellent gastightness at high temperatures. Hence, using the powder filler layer containing no auxiliary filler in addition to the powder filler layer containing the auxiliary filler brings the effect of assuring excellent watertightness and gastightness at high temperatures. Preferred embodiments of the present invention will be explained hereinafter with reference to attached drawings.

First Embodiment

Figure 2:
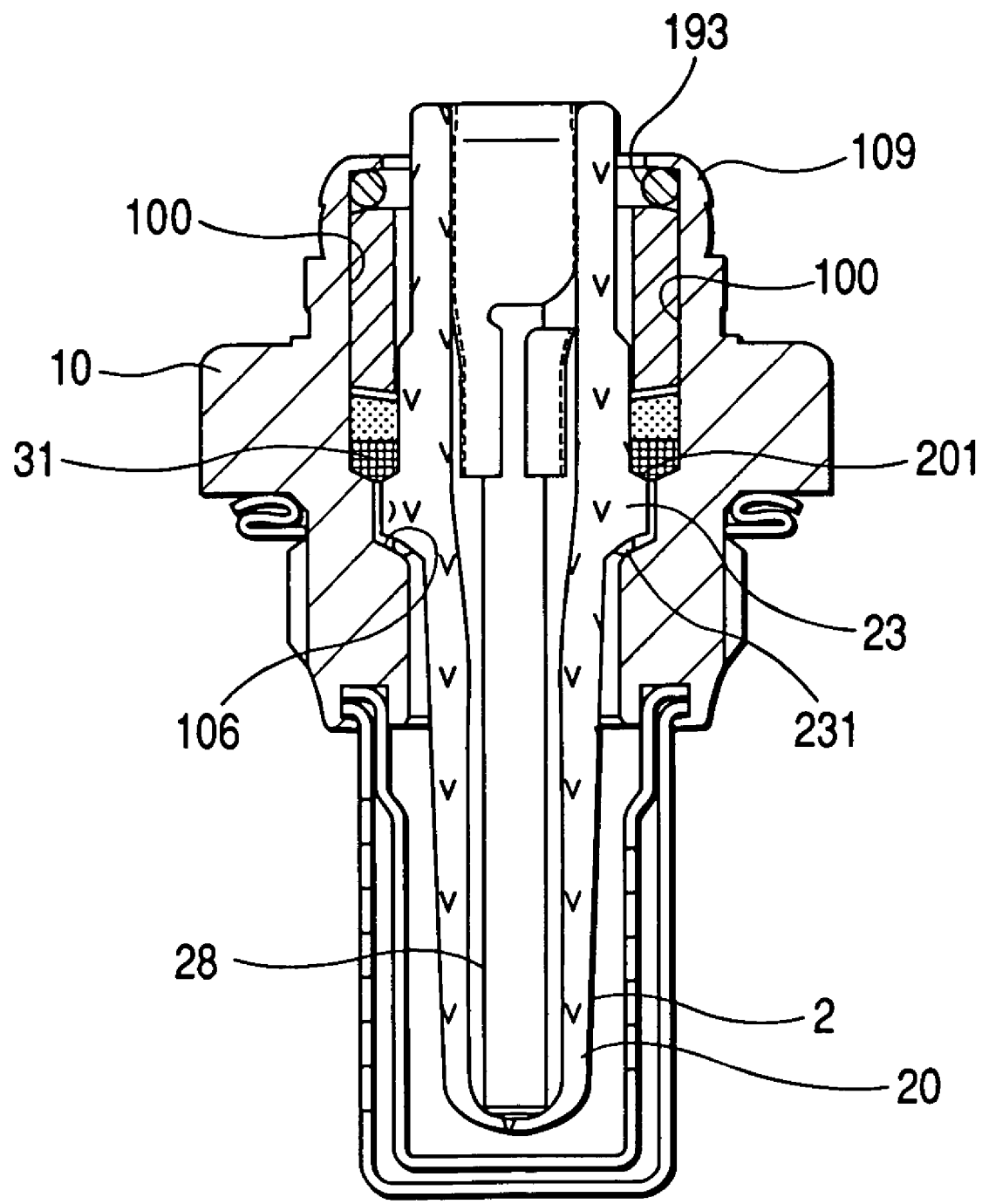
FIG. 2 is a vertical cross-sectional view showing an essential part of the gas sensor in accordance with the first embodiment of the present invention.
Figure 3:
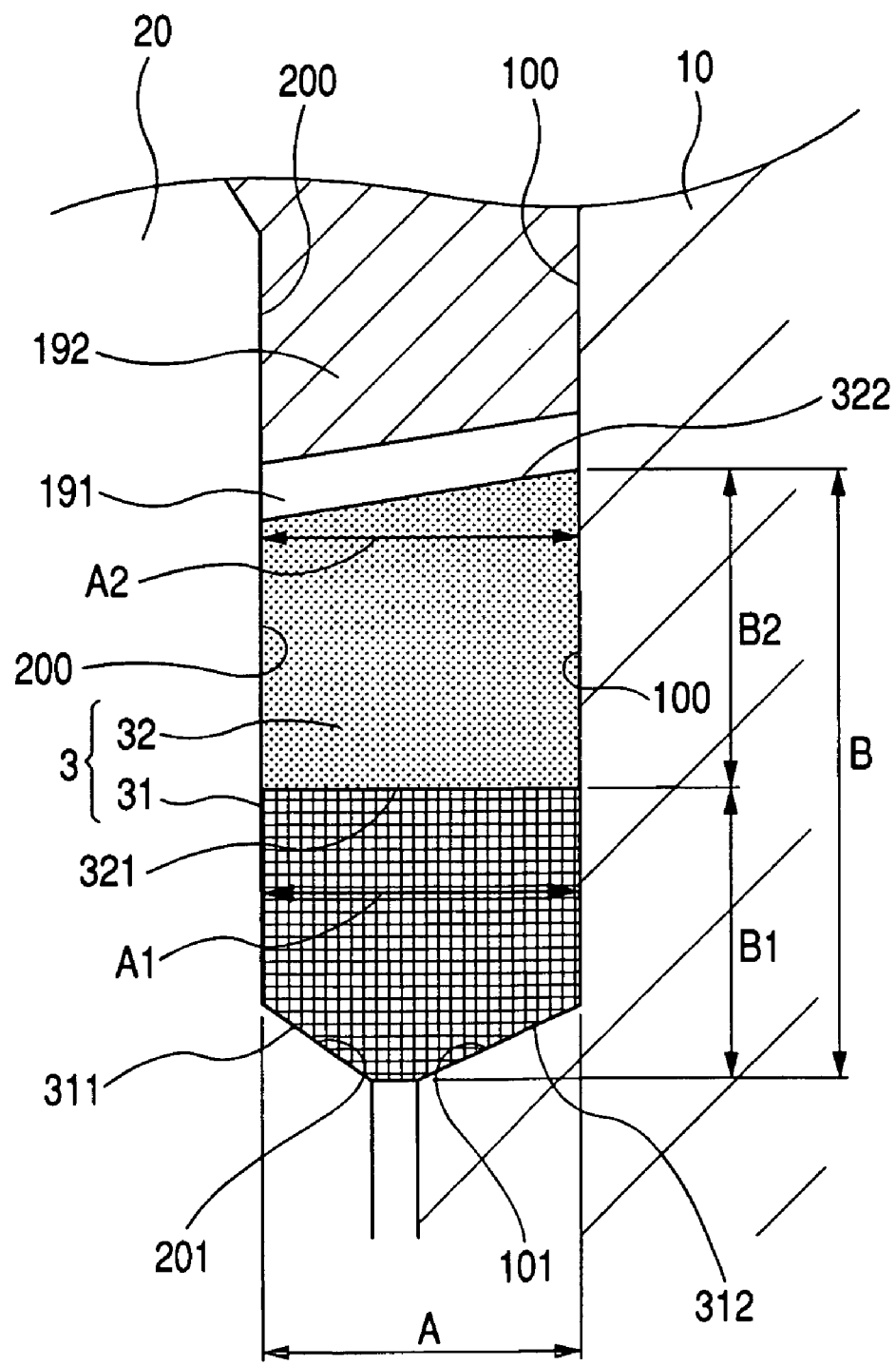
FIG. 3 is an enlarged cross-sectional view showing first and second powder filler layers in accordance with the first embodiment of the present invention.

A preferred embodiment of the present invention will be explained with reference to FIGS. 1 to 8. FIG. 1 shows a gas sensor 1 in accordance with this embodiment, which includes a sensor element 2 inserted in a cylindrical housing 10, a measured gas cover 11 provided at a distal end side of the housing 10 to cover a distal end side of the sensor element 2, and an atmospheric air cover 12 provided at a proximal end side of the housing 10 to cover a proximal end side of the sensor element 2. Furthermore, as shown in FIG. 3, the gas sensor 1 includes a sealing member 3 consisting of first and second powder filler layers 31 and 32 disposed between the sensor element 2 and the housing 10. Thus, a clearance between an inside surface 100 of the housing 10 and an outside surface 200 of the sensor element 2 is gastightly sealed by the sealing member 3.

Hereinafter, the gas sensor 1 in accordance with the first embodiment will be explained in more detail. As shown in FIGS. 1 to 3, the gas sensor 1 has the measured gas cover 11 disposed at the distal end side of the cylindrical housing 10 and the atmospheric air cover 12 disposed at the proximal end side of the cylindrical housing 10. The measured gas cover 11 has a double-layer arrangement consisting of an outer cover 111 and an inner cover 112. The inside space of the inner cover 112 forms the measured gas environment 110. The distal end side of the sensor element 2 is exposed in the measured gas environment 110 to measure the concentration of a specific gas contained in the measured gas (e.g. exhaust gas of an automotive internal combustion engine). The atmospheric air cover 12 includes a main cover member 121 and an outside cover member 122. The outside cover member 122 is fixed by caulking around the proximal end side of the main cover member 121 via a water-repellent filter 125. The inside space of the main cover member 121 forms the atmospheric air environment 120. The proximal end side of the sensor element 2 is exposed in the atmospheric air environment 120. Air is stored in the atmospheric air environment 120 as a reference gas to be introduced into a later-described atmospheric air chamber 28 of the sensor element 2. Furthermore, the main cover member 121 and the outside cover member 122 have air holes 123 and 124 for introducing the ambient air into the atmospheric air environment 120.

An atmospheric air side insulator 13, supported by a disc spring 131, is placed inside the main cover member 121. A plurality of connecting terminals 14 are provided inside the atmospheric air side insulator 13 to connect later-described signal output terminals 211 and 221 to lead wires 15 and also connect heater leads 291 to lead wires 15. Furthermore, the lead wires 15 are inserted in an elastic insulating member 16 provided at the proximal end side of the atmospheric air side insulator 13 and inside the proximal end side of the main cover member 121.

The sensor element 2 of this embodiment includes a cup-shaped solid electrolyte 20, a pair of electrodes (not shown in the drawings) provided on inside and outside surfaces of the solid electrolyte 20, the atmospheric air chamber 28 formed inside the solid electrolyte 20, and a heater 29 placed in the atmospheric air chamber 28. The signal output terminals 211 and 221 are provided at the proximal end side of the sensor element 2 and electrically connected to the electrodes (not shown in the drawings) of the sensor element 2. Furthermore, heater leads 291 are provided at the proximal end side of the heater 29 and electrically connected to a heating element (not shown) embedded in the heater 29. An annular protrusion 23, protruding outward in the radial direction, is provided on the outside surface 200 of the sensor element 2. The sensor element 2 has an end surface 231 at the distal end side of the protrusion 23. The housing 10 has a support surface 106 (refer to FIG. 2) provided on the inside surface 100. The end surface 231 of the sensor element 2 is supported by the support surface 106 of the housing 10.

Furthermore, as shown in FIGS. 2 and 3, the first and second powder filler layers 31 and 32 are disposed in a space defined by an inside inclined surface 201 of the protrusion 23 formed at the proximal end side thereof, an outside inclined surface 101 of the housing 10 formed on its inside surface 100, the outside surface 200 of the solid electrolyte 20, and the inside surface 100 of the housing 10. The first powder filler layer 31 is positioned closer to the distal end side than the second powder filler layer 32. A packing member 191 is positioned on a proximal end surface 322 of the second powder filler layer 32. An insulator 192 is disposed on the packing member 191. A metallic ring 193 is disposed on the insulator 192. A proximal end side 109 of the housing 10 is caulked inward to press and hold the metallic ring 193 from above. Thus, the insulator 192, the packing member 191, and the first and second powder filler layers 31 and 32 are fixed in an annular clearance between the solid electrolyte 20 and the housing 10.

As shown in FIG. 3, the first powder filler layer 31 has a bottom surface at its distal end side. The bottom surface of the first powder filler layer 31 has two inclined surfaces 312 and 311. The inclined surface 312 fits the outside inclined surface 101 provided on the inside surface 100 of the housing 10. The inclined surface 311 fits the inside inclined surface 201 provided on the outside surface 200 of the solid electrolyte 20. Thus, the first powder filler layer 31 has a sharp-pointed distal end shape. The width of the first powder filler layer 31, in the radial direction, decreases as it approaches the distal end. The second powder filler layer 32 has a distal end surface 321 which is substantially flat. Furthermore, the second powder filler layer 32 has a proximal end surface 322 descending in radial direction from the housing 10 to the sensor element 2. Furthermore, both of the first and second powder filler layers 31 and 32 are made of talc powders. As is well known, talc is of clay minerals and is a natural material containing MgO and $SiO_2$ as the main components. The first and second powder filler layers 31 and 32 are made of the same talc powders.

Figure 4A:
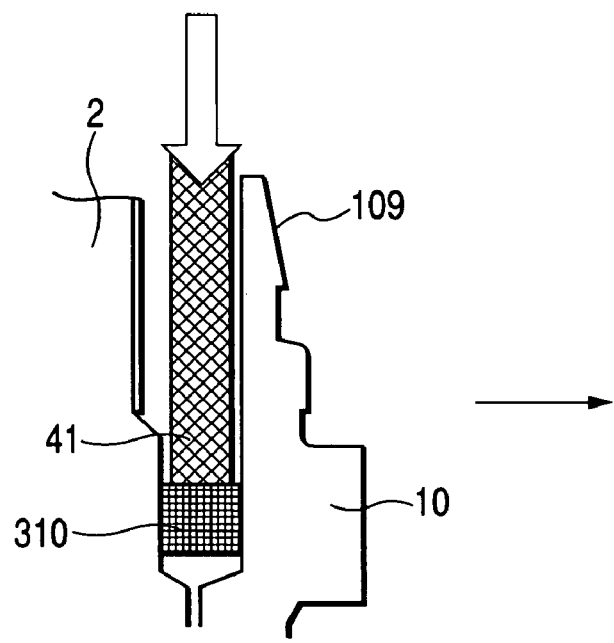
FIGS. 4A and 4B are cross-sectional views explaining sequential processes for disposing and pressing a first temporary molded article in accordance with the first embodiment of the present invention.
Figure 8:
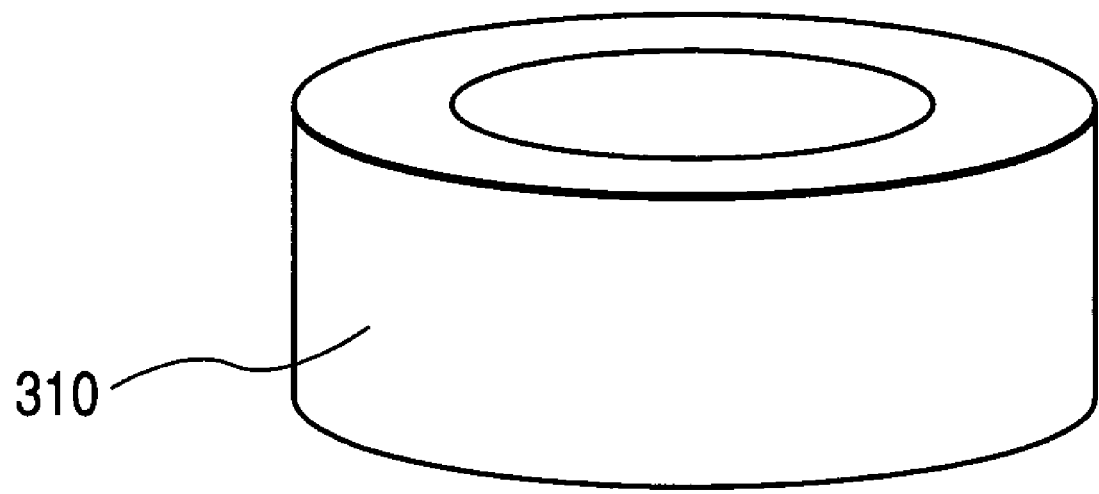
FIG. 8 is a perspective view showing the temporary molded article in accordance with the first embodiment of the present invention.

Next, the processes for forming the first and second powder filler layers 31 and 32 will be explained. First of all, the sensor element 2 is inserted in the housing 10. Next, as shown in FIG. 4A, a first temporary molded article 310 to be formed into the first powder filler layer 31 is disposed between the sensor element 2 and the housing 10. The first temporary molded article 310, as shown in FIG. 8, has an annular body. This annular body is formed by adding an adequate amount of water, if necessary, to talc powders and then molding the talc powders in the annular molding dies. Then, the molded talc powders are configured into an annular body by using a press machine. Regarding the water added to the talc powders, it is preferable to dry it out after the talc powders are molded into the annular body or assembled into the housing 10.

Figure 4B:
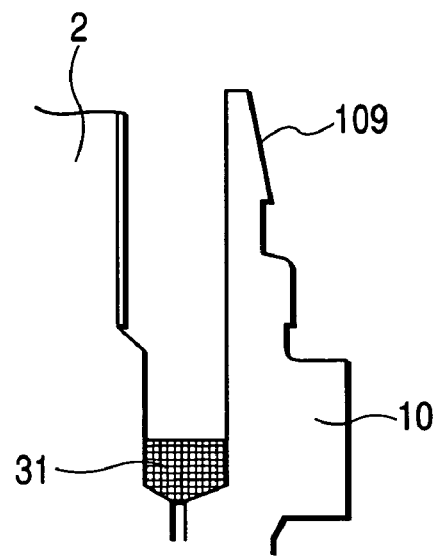
Figure 5:
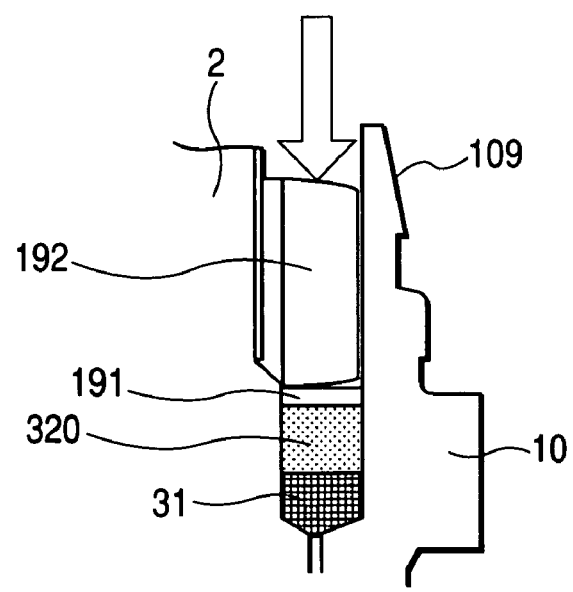
FIG. 5 is a cross-sectional view explaining a process of pressing a second temporary molded article together with a packing member, and an insulator in accordance with the first embodiment of the present invention.

Then, as shown in FIG. 4A, a cylindrical die 41 is lowered from above into the clearance between the sensor element 2 and the housing 10 to press the first temporary molded article 310. Thus, as shown in FIG. 4B, the first temporary molded article 310 is pressed and deformed into the first powder filler layer 31. Next, as shown in FIG. 5, a second temporary molded article 320 to be formed into the second powder filler layer 32 is disposed on the first powder filler layer 31. Furthermore, the packing member 191 and the insulator 192 are successively disposed on the first powder filler layer 31. Then, a cylindrical die (not shown) is lowered from above to press the second temporary molded article 320 via the insulator 192. Thus, the second temporary molded article 320 is pressed and deformed into the second powder filler layer 32. Regarding the pressing operation performed for forming the second powder filler layer 32, it is possible to press the second temporary molded article 320 before disposing the insulator 192 and the packing member 191. Alternatively, it is possible to simultaneously press both of the first temporary molded article 310 and the second temporary molded article 320 disposed between the sensor element 2 and the housing 10, to obtain the first and second powder filler layers 31 and 32 at the same time.

Figure 6:
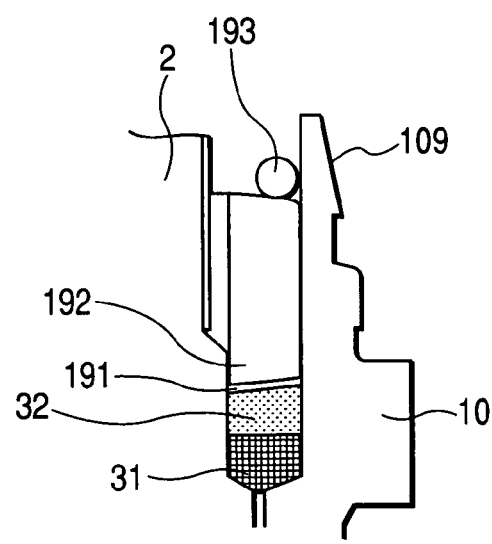
FIG. 6 is a cross-sectional view showing a metallic ring disposed on the insulator in accordance with the first embodiment of the present invention.
Figure 7A:
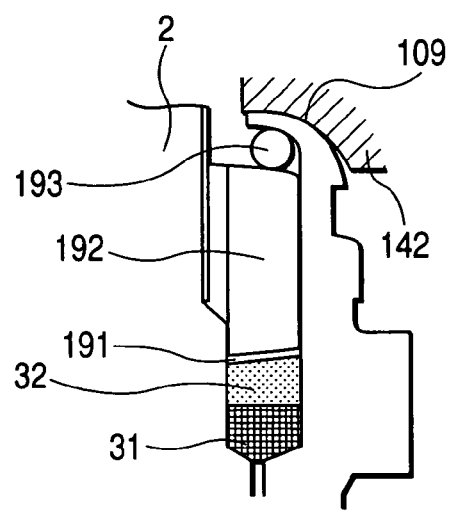
FIGS. 7A and 7B are cross-sectional views explaining sequential processes for caulking the metallic ring together with the insulator in accordance with the first embodiment of the present invention.
Figure 7B:
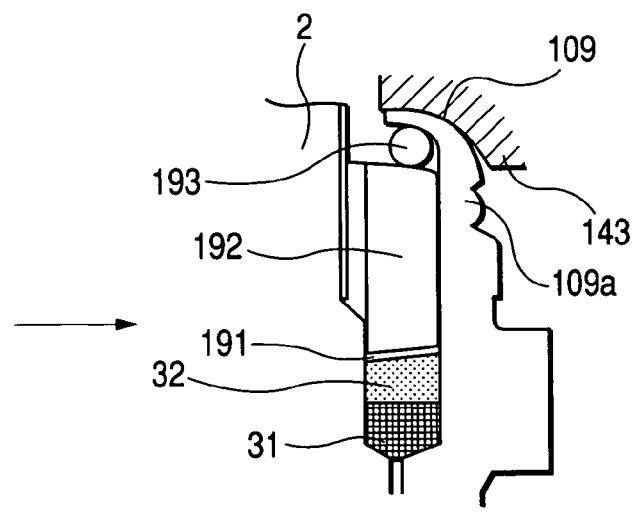

Next, as shown in FIG. 6, the metallic ring 193 is disposed on the insulator 192. Then, as shown in FIG. 7A, a cold caulking die 142 is disposed at the proximal end side of the housing 10 to deform the proximal end side 109 of the housing 10 inward so as to fixedly hold the metallic ring 193. Furthermore, as shown in FIG. 7B, a hot caulking die 143 is disposed at the proximal end side of the housing 10 to cause a hot caulking portion 109a of the housing 10 to buckle during the hot caulking operation. Through the above processes, both the first and the second powder filler layers 31 and 32 are firmly fixed so as to completely seal the clearance between the sensor element 2 and the housing 10. Thereafter, the remaining constituent components are assembled in a predetermined order to obtain the gas sensor 1 of this embodiment.

The gas sensor 1 according to this embodiment includes the sealing member 3 consisting of the first and second powder filler layers 31 and 32 disposed in the clearance between the sensor element 2 and the housing 10. Providing the first and second powder filler layers 31 and 32 brings the effect of enhancing the sealing properties of the gas sensor 1 to surely separate or isolate the measured gas environment 110 formed inside the measured gas cover 11 from the atmospheric air environment 120 formed inside the atmospheric air cover 12. Thus, the gas sensor 1 of this embodiment possesses excellent watertightness and accordingly can surely block the liquid entering from the measured gas environment 110. Furthermore, the sealing member 3 has a uniform and high density. The density of the sealing member 3 does not vary so easily and accordingly it becomes possible to maintain long-lasting and excellent sealing properties. Furthermore, according to this embodiment, the sealing member 3 can be manufactured by using a simple manufacturing method including a step of temporarily molding the powder material and a step of pressing the temporary molded article. Thus, no special apparatus is required to manufacture the sealing member, and accordingly the sealing member can be easily manufactured.

Furthermore, the first and second powder filler layers 31 and 32 of this embodiment are made of talc. As the molding of talc can be done at room temperatures, thermal energy can be saved. Furthermore, the talc particles are scaly particles having a layered structure. When the talc particles are pressed, they cause cleavage in the layered direction while maintaining the layered structure of the scaly particles. Furthermore, as the talc particles are sufficiently soft (Mohs hardness=1), the scaly particles can deform so as to eliminate the clearances remaining between the talc particles before obtaining the powder filler layers. Therefore, the specific gravity can be increased and accordingly excellent sealing properties can be easily obtained.

To evaluate the gas sensor in accordance with the first embodiment of the present invention, the inventors have prepared various samples and conducted various tests on these samples. More specifically, the inventors have evaluated gastightness and/or watertightness in relation to sizes of respective powder filler layers arranging the sealing member. A total of twenty-five (25) samples were prepared and these samples were roughly classified into three groups with respect to the layer arrangement of the sealing member.

More specifically, the first group (i.e. samples 1 to 4) is characterized in that the sealing member has a single-layer arrangement. The second group (i.e. samples 5 to 21) is characterized in that the sealing member has a double-layer arrangement. And, the third group (i.e. samples 22 to 25) is characterized in that the sealing member has a triple-layer arrangement. In this respect, the test samples 1 to 4 have the conventional arrangement. The test samples 5 to 21 have the arrangement of the first embodiment. Regarding the arrangement other than the sealing member, respective samples 1 to 25 are substantially identical with the gas sensor in accordance with the first embodiment. Furthermore, regarding the composition of the powder filler layers and the manufacturing method, there is no substantial difference between the test samples 1 to 25 and the gas sensor of the first embodiment.

The test samples 5 to 21 have the sealing member of the double-layer arrangement as shown in FIG. 3. In the gas sensor shown in FIG. 3, it is now assumed that 'A' represents a maximum width of the sealing member 3, 'B' represents a maximum thickness of the sealing member 3, 'A1' represents a maximum width of the first powder filler layer 31, 'B1' represents a maximum thickness of the first powder filler layer 31, 'A2' represents a maximum width of the second powder filler layer 32, and 'B2' represents a maximum thickness of the second powder filler layer 32. Furthermore, the widths A1 and A2 are mutually identical and are set to 2 mm, and accordingly the maximum width A is 2 mm. Here, the maximum width is the length measured along the radial direction of the gas sensor. The maximum thickness is the length measured along the axial direction of the gas sensor which has substantially a rotor body.

The test samples 1 to 4 have the sealing member of the single-layer arrangement including only one (i.e. first) powder filler layer (not shown in the drawings). Therefore, the maximum width A of the sealing member is identical with the maximum width 'A1' of the first powder filler layer. The maximum thickness B of the sealing member is identical with the maximum thickness 'B1' of the first powder filler layer. Furthermore, the widths A1 and A are set to 2 mm. The samples 22 to 25 have the sealing member of the triple-layer arrangement consisting of first to third powder filler layers (not shown in the drawings). Like the arrangement shown in FIG. 3, the samples 22 to 25 have the first powder filler layer having the maximum width 'A1' and the maximum thickness 'B1', the second powder filler layer having the maximum width 'A2' and the maximum thickness 'B2', and the third powder filler layer having the maximum width 'A3' and the maximum thickness 'B3'. The sealing member has the maximum width 'A' and the maximum thickness 'B'. Furthermore, the widths A1, A2, and A3 are mutually identical and are set to 2 mm, and accordingly the maximum width A is 2 mm.

The sealing properties of the sealing member in respective test samples were measured according to the following method. First, each sample of the gas sensor was heated from the distal end side thereof, so that the temperatures of the inside inclined surface and the outside inclined surface of the first powder filler layer (in the case of respective samples 1 to 4, only one powder filler layer arranging the sealing member) increase up to 400° C. and the temperature of the elastic insulating member (indicated by reference numeral 16 in FIG. 1) positioned at the proximal end side of the gas sensor reaches 250° C. Then, 500 cc of water was sprayed onto the heated sensor body for twenty (20) seconds. Such a heating and cooling operation was repeated 500 cycles for each sample of the gas sensor. Then, the sealing properties of each test sample were evaluated by using the following method.

The housing positioned at the distal end side of the gas sensor was inserted into a tube. A pressure of 1 MPa (10 atm) was applied to the housing in the tube to increase the pressure of the measured gas environment. In this condition, a gas amount leaking from the measured gas environment via the sealing member, the packing member, the insulator, and the metallic ring to the atmospheric air environment was measured. In a case that the gas sensor is placed into an exhaust pipe of an automotive engine to measure a gas concentration of the exhaust gas, the inside pressure of the exhaust pipe is usually lower than 1 MPa. Thus, when a leak amount in this test is equal to or less than 10 ml/min, the test sample can be regarded as having sufficient sealing properties as a gas sensor installable in the exhaust pipe of an automotive engine. Considering this fact, the evaluation results with respect to gastightness of respective samples 1 to 25 were classified into four categories. More specifically, as shown in Table 1, x indicates the samples having a leak amount greater than 10 ml/min; ○ represents the samples having a leak amount greater than 5 ml/min and not greater than 10 ml/min; ⊚ represents the samples having a leak amount greater than 2.5 ml/min and not greater than 5 ml/min; and ☆ represents the samples having the leak amount not greater than 2.5 ml/min. This measurement was conducted in the high-temperature condition that the first powder filler layer is heated up to 550° C.

Next, the inside space of the measured gas cover of the gas sensor was filled with stain solution. Then, the maximum depth of the stain solution immersed into the sealing member from the measured gas environment was measured after twelve (12) hours has passed. When the immersion depth of the stain solution is small, the test sample has excellent watertightness and can be regarded as having sufficient sealing properties as a gas sensor installable in the exhaust pipe of an automotive engine. Considering this fact, the evaluation results with respect to watertightness of respective samples 1 to 25 were classified into four categories. More specifically, the watertightness of respective samples 1 to 25 was evaluated in terms of a ratio of L/B, where 'L' represents the immersion depth of the stain solution and 'B' represents the maximum height of the sealing member. As shown in Table 1, x indicates the samples having the ratio L/B greater than 70%; ○ represents the samples having the ratio L/B greater than 50% and not greater than 70%; ⊚ represents the samples having the ratio L/B greater than 25% and not greater than 50%; and ☆ represents the samples having the ratio L/B not greater than 25%. This measurement was conducted at room temperatures.

Table 1 shows the result of above evaluation tests.

TABLE 1

| Sample No. | Seal member | B/A | B1/A1 | B2/A2 | B3/A3 | Gastightness (ml/min) | Evaluation for gastightness | Watertightness (%) | Evaluation for watertightness |
|---|---|---|---|---|---|---|---|---|---|
| 1 | Single | 0.8 | — | — | — | 23 | X | 100 | X |
| 2 | layer | 1.5 | — | — | — | 15 | X | 75 | X |
| 3 | | 3.0 | — | — | — | 11 | X | 80 | X |
| 4 | | 5.0 | — | — | — | 16 | X | 85 | X |
| 5 | Double | 0.6 | 0.3 | 0.3 | — | 15 | X | 75 | X |
| 6 | layer | 0.8 | 0.4 | 0.4 | — | 10 | ○ | 65 | ○ |
| 7 | | 1.0 | 0.5 | 0.5 | — | 5 | ⊚ | 45 | ⊚ |
| 8 | | 1.2 | 0.6 | 0.6 | — | 1.5 | ☆ | 25 | ☆ |
| 9 | | 2.0 | 1.0 | 1.0 | — | 1 | ☆ | 15 | ☆ |
| 10 | | 3.0 | 1.5 | 1.5 | — | 2.5 | ☆ | 30 | ⊚ |
| 11 | | 4.0 | 2.0 | 2.0 | — | 4 | ⊚ | 40 | ⊚ |
| 12 | | 5.0 | 2.5 | 2.5 | — | 4.5 | ⊚ | 40 | ⊚ |
| 13 | | 6.0 | 3.0 | 3.0 | — | 8 | ○ | 55 | ○ |
| 14 | | 1.0 | 0.6 | 0.4 | — | 4.5 | ⊚ | 35 | ⊚ |
| 15 | | 2.0 | 1.5 | 0.5 | — | 2 | ☆ | 45 | ⊚ |
| 16 | | 3.0 | 2.0 | 1.0 | — | 3 | ⊚ | 45 | ⊚ |
| 17 | | 4.0 | 3.0 | 1.0 | — | 4.5 | ⊚ | 50 | ⊚ |
| 18 | | 1.0 | 0.4 | 0.6 | — | 5 | ⊚ | 50 | ⊚ |
| 19 | | 2.0 | 0.5 | 1.5 | — | 3 | ⊚ | 35 | ⊚ |
| 20 | | 3.0 | 1.0 | 2.0 | — | 3 | ⊚ | 30 | ⊚ |
| 21 | | 4.0 | 1.0 | 3.0 | — | 3.5 | ⊚ | 35 | ⊚ |
| 22 | Triple | 3.0 | 1.0 | 1.0 | 1.0 | 1.5 | ☆ | 15 | ☆ |
| 23 | layer | 4.0 | 1.3 | 1.3 | 1.3 | 1.5 | ☆ | 20 | ☆ |
| 24 | | 5.0 | 1.7 | 1.7 | 1.7 | 3.5 | ⊚ | 35 | ⊚ |
| 25 | | 6.0 | 2.0 | 2.0 | 2.0 | 6 | ○ | 40 | ⊚ |

First, regarding the samples 1 to 4 having the sealing member consisting of a single powder filler layer, both of gastightness and watertightness were unsatisfactory as evaluated by X. Second, regarding the samples 6 to 21 having the sealing member consisting of two powder filler layers, both the gastightness and watertightness were excellent as evaluated by ○, ⊚, or ☆. Regarding sample 5, its gastightness and watertightness are superior to those of sample 1, although the ratio B/A of sample 5 is smaller than that of sample 1. Accordingly, it is confirmed that employing the double-layer arrangement for the sealing member brings the effects of improving both gastightness and watertightness. Furthermore, the samples 7 to 12 and 14 to 21 satisfying the condition 1.0 ≦B/A 5.0 were evaluated by ⊚ or ☆ and accordingly can assure further excellent gastightness and watertightness. Furthermore, the samples 8 and 9 satisfying the conditions 0.6 ≦B1/A≦1.3 and 0.6 ≦B2/A2≦1.3 evaluated by ☆ and accordingly can assure more excellent gastightness and watertightness. Regarding the samples 21 to 25 having the sealing member consisting of three powder filler layers, both-of the gastightness and watertightness were excellent as evaluated by ○, ⊚, or ☆. Furthermore, the samples 22 to 24 satisfying the conditions $1.0 \leq B/A \leq 5.0$ were evaluated by ⊚ or ☆ and accordingly can assure further excellent gastightness and watertightness.

Figure 9:
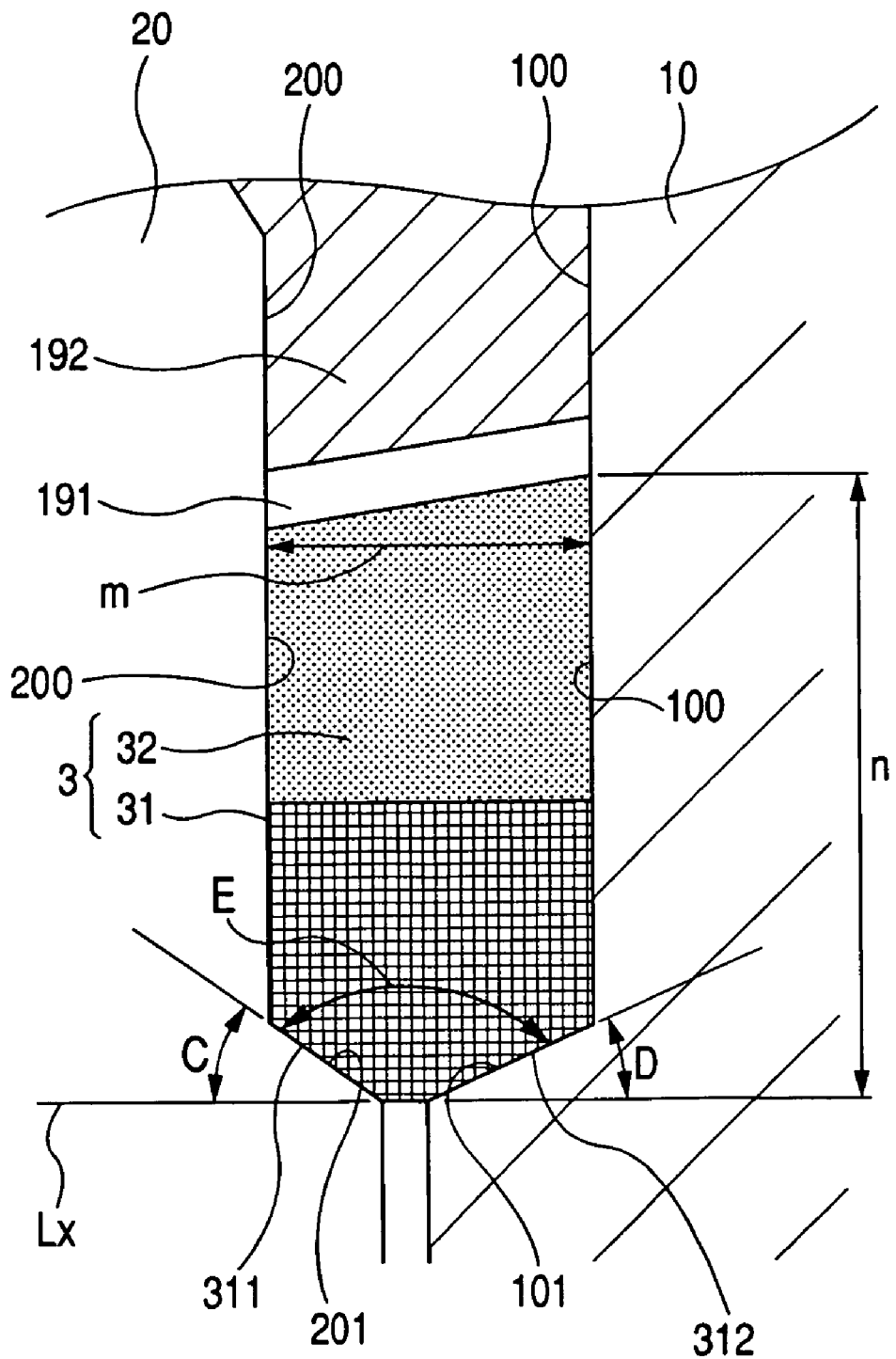
FIG. 9 an enlarged cross-sectional view explaining various angles defining the inside inclined surface and the outside inclined surface in accordance with the first embodiment of the present invention.

Furthermore, the inventors have further conducted the following tests to evaluate gastightness and watertightness of the gas sensor in accordance with the first embodiment of the present invention in relation to angles of various portions of the gas sensor. More specifically, in the gas sensor in accordance with the first embodiment, the first powder filler layer 31 positioned closest to the distal end side of the gas sensor is brought into contact with the outside inclined surface 101 descending from the housing 10 toward the sensor element 2 and also brought into contact with the inside inclined surface 201 descending from the sensor element 2 toward the housing 10. It is now assumed that 'C' represents the angle formed between the inside inclined surface 201 and a line normal to the axial direction of the gas sensor, 'D' represents the angle formed between the outside inclined surface 101 and the line normal to the axial direction of the gas sensor, and 'E' represents the angle formed between the inside inclined surface 201 and the outside inclined surface 101. More specifically, as shown in FIG. 9, when 'Lx' represents a straight line parallel to the radial direction of the gas sensor, 'C' represents the angle formed between the straight line Lx and the inside inclined surface 201, 'D' represents the angle formed between the straight line Lx and the outside inclined surface 101, and 'E' represents the angle formed between the inside inclined surface 201 and the outside inclined surface 101.

The inventors prepared test samples 26 to 50. The test samples 26, 27, and 28 have the conventional sealing member consisting of a single powder filler layer. The rest of the arrangement of respective samples 26, 27, and 28 is identical with the gas sensor according to the first embodiment of the present invention. Furthermore, these samples 26, 27 and 28 are identical with the gas sensor of the first embodiment in the composition of the powder filler as well as in the manufacturing method. The single powder filler layer of respective samples 26, 27 and 28 is brought into contact at its bottom surface with the inside inclined surface and the outside inclined surface as shown in FIG. 9.

The samples 26 to 50 are gas sensors each having the sealing member consisting of two powder filler layers according to the first embodiment of the present invention and are differentiated from each other in the angles C, D, or E. Furthermore, regarding the samples 26 to 50, the sealing member has the width "m" of 2 mm and the axial length "n" of 6 mm (refer to FIG. 9). In each test sample, sealing properties of the sealing member 3 were measured according to the above-described method. Table 2 shows the result of the above evaluation tests.

TABLE 2

| Sample No. | Seal member | C | D | E | Gastightness (ml/min) | Evaluation for gastightness | Watertightness (%) | Evaluation for watertightness |
|---|---|---|---|---|---|---|---|---|
| 26 | Single | 60 | 30 | 90 | 16 | X | 100 | X |
| 27 | layer | 30 | 30 | 120 | 11 | X | 80 | X |
| 28 | | 0 | 0 | 180 | 8 | ○ | 75 | X |
| 29 | Double | 60 | 60 | 60 | 8 | ○ | 70 | ○ |
| 30 | layer | 60 | 30 | 90 | 6.5 | ○ | 60 | ○ |
| 31 | | 60 | 0 | 120 | 5.5 | ○ | 55 | ○ |
| 32 | | 50 | 0 | 130 | 5 | ⊚ | 40 | ⊚ |
| 33 | | 40 | 0 | 140 | 3 | ⊚ | 35 | ⊚ |
| 34 | | 30 | 0 | 150 | 2 | ☆ | 20 | ☆ |
| 35 | | 30 | 30 | 120 | 2.5 | ☆ | 30 | ⊚ |
| 36 | | 30 | 60 | 90 | 6 | ○ | 65 | ○ |
| 37 | | 0 | 60 | 120 | 5 | ⊚ | 60 | ○ |
| 38 | | 0 | 50 | 130 | 4.5 | ⊚ | 30 | ⊚ |
| 39 | | 0 | 40 | 140 | 3.5 | ⊚ | 30 | ⊚ |
| 40 | | 0 | 30 | 150 | 2 | ☆ | 15 | ☆ |
| 41 | | 0 | 0 | 180 | 1 | ☆ | 10 | ☆ |
| 42 | | 40 | 40 | 100 | 4.5 | ⊚ | 55 | ○ |
| 43 | | 40 | 30 | 110 | 4.5 | ⊚ | 55 | ○ |
| 44 | | 40 | 20 | 120 | 4 | ⊚ | 35 | ⊚ |
| 45 | | 30 | 40 | 110 | 4 | ⊚ | 60 | ○ |
| 46 | | 20 | 40 | 120 | 4.5 | ⊚ | 40 | ⊚ |
| 47 | | 10 | 50 | 120 | 4 | ⊚ | 40 | ⊚ |
| 48 | | 20 | 50 | 110 | 5 | ⊚ | 60 | ○ |
| 49 | | 50 | 10 | 120 | 4 | ⊚ | 30 | ⊚ |
| 50 | | 50 | 20 | 110 | 4 | ⊚ | 65 | ○ |

As apparent from Table 2, the samples 26 to 28 having the conventional sealing member consisting of a single powder filler layer were unsatisfactory in either gastightness or watertightness and were evaluated by X. On the other hand, the samples 29 to 50 having the sealing member consisting of two powder filler layers showed excellent gastightness and watertightness and were evaluated by ○, ⊚, or ☆. Especially, the samples 32 to 35, 38 to 41, 44, 46, 47, and 49, each satisfying the relationships of $0° \leq C \leq 50°$, $0° \leq D \leq 50°$, and $120° \leq E \leq 180°$, were evaluated by ⊚ or ☆ and accordingly can assure further excellent gastightness and watertightness.

Second Embodiment

Figure 10:
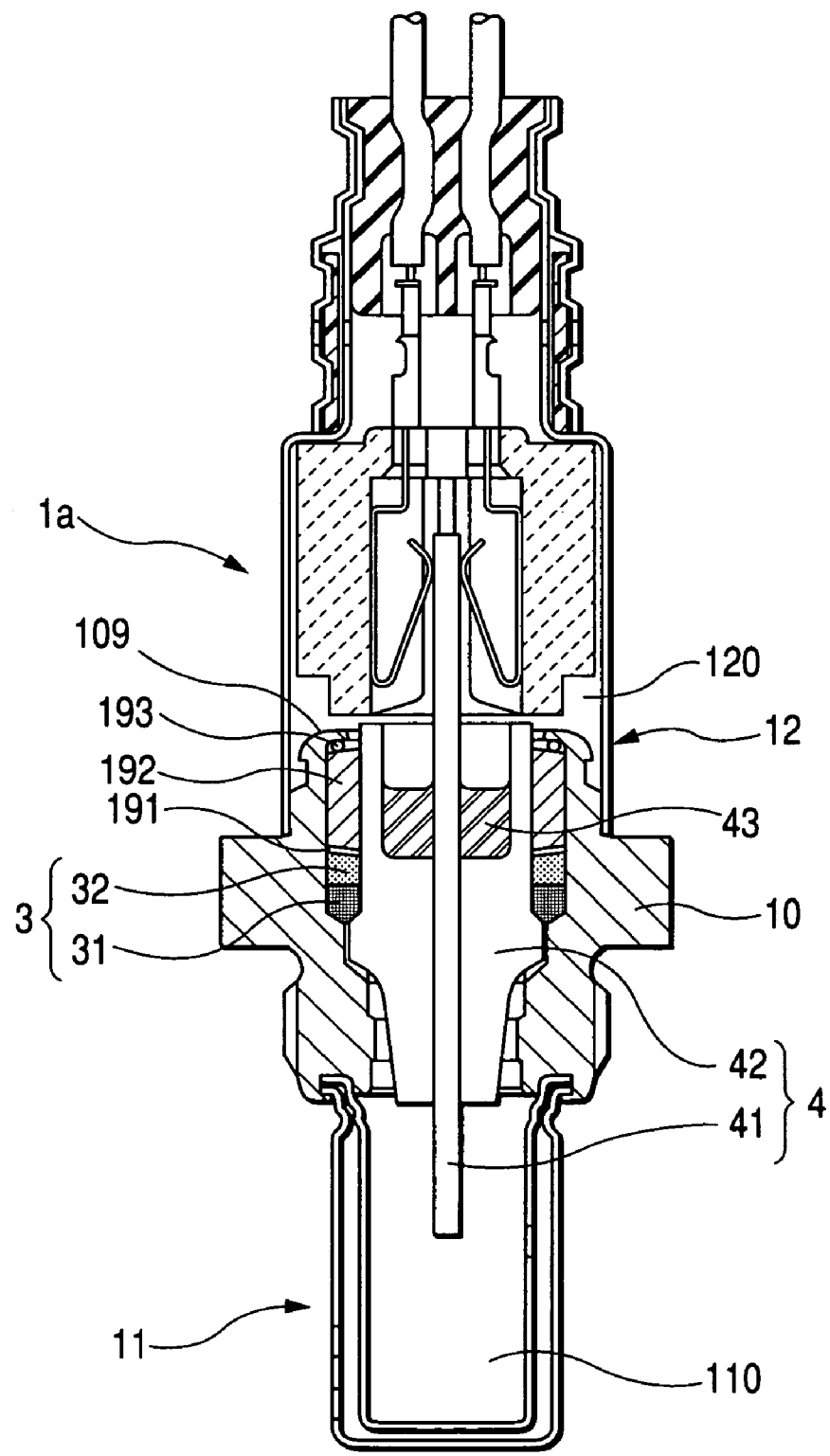
FIG. 10 is a vertical cross-sectional view showing an overall arrangement of a gas sensor in accordance with a second embodiment of the present invention.

This embodiment, as shown in FIG. 10, discloses a gas sensor 1a including an element assembly 4 inserted in the cylindrical housing 10. The element assembly 4 is an assembly of a sensor element 41 and a cylindrical insulating tube 42 which are integrated together so that the cylindrical insulating tube 42 surrounds an outer cylindrical surface of the sensor element 41. Furthermore, the gas sensor 1a includes a measured gas cover 11 provided at a distal end side of the housing 10 to cover a distal end side of the sensor element 41 and an atmospheric air cover 12 provided at a proximal end side of the housing 10 to cover a proximal end side of the sensor element 41.

The gas sensor 1a according to this embodiment has the element assembly 4 including the plane multilayered sensor element 41 inserted in the insulating tube 42, with a glass seal member 43 disposed between the sensor element 41 and the insulating tube 42 to provide a gastight sealing between them. Furthermore, like the first embodiment, a sealing member 3 consisting of first and second powder filler layers 31 and 32 is disposed in a clearance between the element assembly 4 and the housing 10. The first powder filler layer 31 is positioned closely to the distal end side compared with the second powder filler layer 32. A packing member 191 is positioned on a proximal end surface of the second powder filler layer 32. An insulator 192 is disposed on the packing member 191. A metallic ring 193 is disposed on the insulator 192. A proximal end side 109 of the housing 10 is caulked inward to press and hold the metallic ring 193 from above. Thus, the insulator 192, the packing member 191, and the first and second powder filler layers 31 and 32 are fixed in an annular clearance between the element assembly 4 and the housing 10. The rest of the arrangement of the gas sensor 1a according to the second embodiment is similar to those of the gas sensor 1 according to the first embodiment. Furthermore, the manufacturing methods explained for the gas sensor 1 of the first embodiment can be equally applied to the gas sensor 1a of the second embodiment.

According to the gas sensor 1a of this embodiment, it becomes possible to surely separate or isolate the measured gas environment 110 formed inside the measured gas cover 11 from the atmospheric air environment 120 formed inside the atmospheric air cover 12. The watertightness can be improved, and accordingly it becomes possible to surely eliminate immersion of the liquid entering from the measured gas environment 110. Furthermore, the density of the sealing member 3 consisting of first and second powder filler layers 31 and 32 becomes uniform and high. The density does not vary so easily and accordingly it becomes possible to maintain long-lasting and excellent sealing properties.

Third Embodiment

Figure 11:
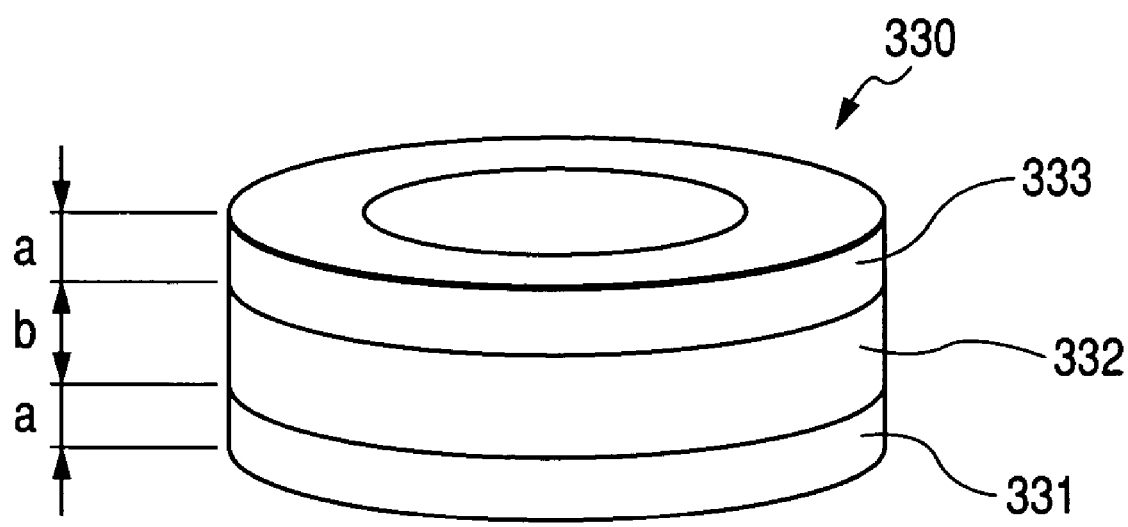
FIG. 11 is a perspective view showing a temporary molded article in accordance with a third embodiment of the present invention.
Figure 12:
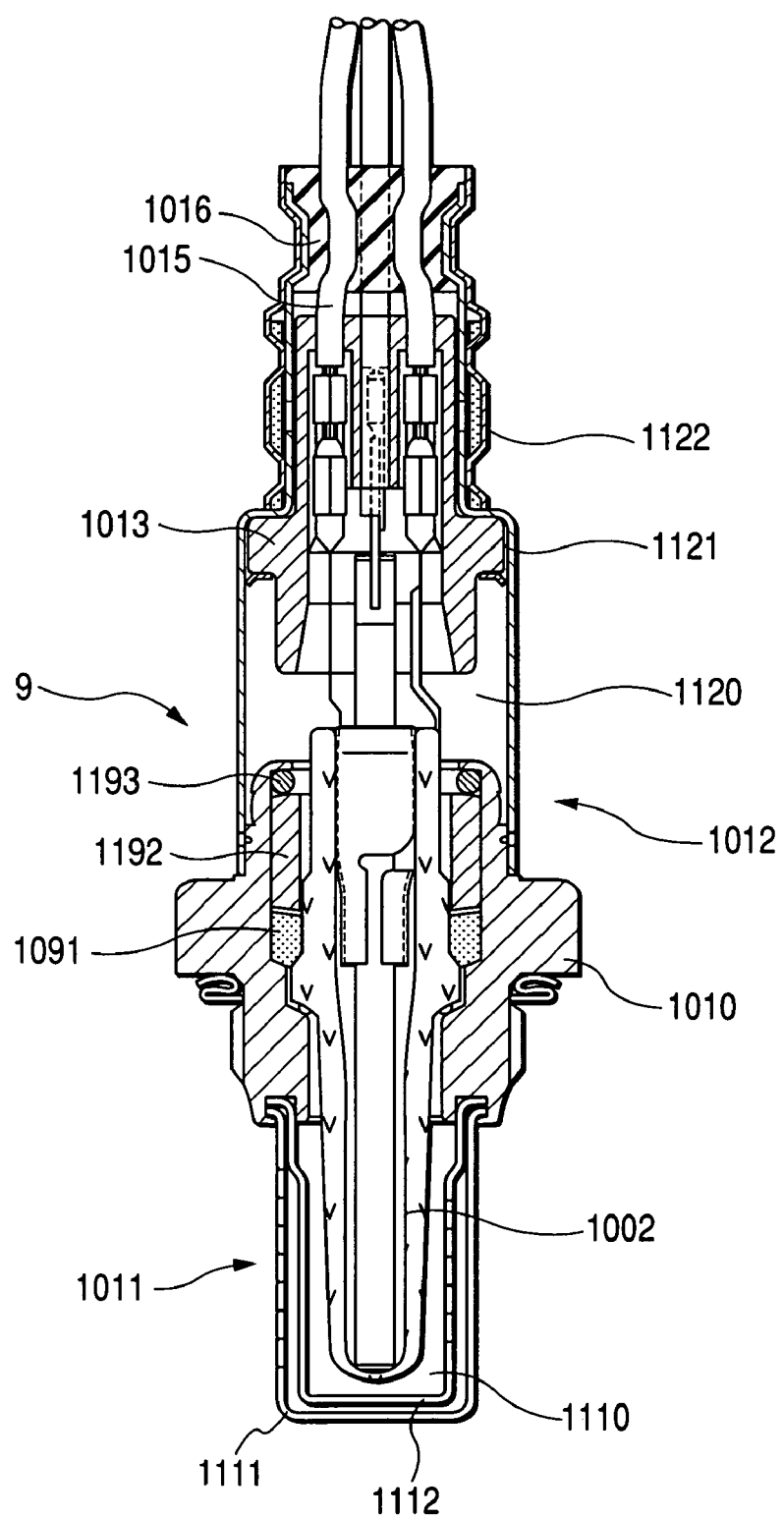
FIG. 12 is a vertical cross-sectional view showing a conventional gas sensor.

This embodiment, as shown in FIG. 11, discloses a temporary molded article 330 to be formed into the sealing member 3, which is manufactured by disposing an odd number of plural layers of different powder materials so as to form a symmetrical laminated structure which is arranged symmetrically in the lamination direction. More specifically, the temporary molded article 330 includes a first layer 331 of first sealing powders, a second layer 332 of second sealing powders, and a third layer 333 of third sealing powders which are laminated in this order. The first layer 331 and the third layer 333 are made of the same sealing powders and have the same thickness 'a'. Furthermore, the second layer 332 is made of sealing powders different from the sealing powders of the first layer 331 and the third layer 333. Furthermore, the second layer 332 has a thickness 'b' which is different from or equal to the thickness 'a' of the first layer 331 and the third layer 333.

According to this embodiment, the temporary molded article 330 can be obtained as a symmetrical product having the same configuration at its distal end side and its proximal end side. Therefore, in the assembling process of the temporary molded article 300 to be disposed between the housing 10 and the sensor element 2 (refer to FIG. 1) or between the housing 10 and the element assembly 4 (refer to FIG. 10), it is unnecessary to carefully check the correct direction of the temporary molded article 300. Namely, it is unnecessary to designate the first layer 331 or the third layer 333 as a portion to be directed to the distal end side, because the temporary molded article 330 can be disposed correctly in either case. Therefore, it becomes possible to improve the efficiency in the assembling work for disposing the temporary molded article 330, and accordingly the productivity of the gas sensor can be improved. Furthermore, this embodiment brings the functions and effects similar to those of the first embodiment.

What is claimed is:

1. A gas sensor comprising:
    a sensor element inserted in a cylindrical housing;
    a measured gas cover provided at a distal end side of said housing to cover a distal end side of said sensor element; and
    an atmospheric air cover provided at a proximal end side of said housing to cover a proximal end side of said sensor element,
    wherein a clearance between an inside surface of said housing and an outside surface of said sensor element is gastightly sealed with a sealing member including a plurality of powder filler layers made of the same material as one another, and
    wherein the powder filler layers directly contact with each other.

2. The gas sensor in accordance with claim 1, wherein said plurality of powder filler layers include predetermined powder material containing particles whose particle sizes are in a range from 80 to 1000 µm by an amount equal to or greater than 80 wt. % of the entire weight.

3. The gas sensor in accordance with claim 1, wherein said plurality of powder filler layers include a first powder filler layer positioned closest to the distal end side of said gas sensor,
    said first powder filler layer contacts with an inside inclined surface provided on an outside surface of said sensor element and inclined from said sensor element to said housing, said first powder filler layer contacts with an outside inclined surface provided on an inside surface of said housing and inclined from said housing to said sensor element, and
    conditions of $0°≦C≦50°$, $0°≦D≦50°$, and $120°≦E≦180°$ are satisfied
    where 'C' represents an angle formed between said inside inclined surface and a line normal to an axial direction of said gas sensor,
    'D' represents an angle formed between said outside inclined surface and said line normal to the axial direction of said gas sensor, and
    'E' represents an angle formed between said inside inclined surface and said outside inclined surface.

4. The gas sensor in accordance with claim 1, further comprising a packing member contacting with an end surface of at least one of said plurality of powder filler layers.

5. The gas sensor in accordance with claim 1, wherein at least one of said plurality of powder filler layers contains an auxiliary filler.

6. The gas sensor in accordance with claim 5, wherein said auxiliary filler is selected from the group consisting of an aqueous solution of primary aluminum phosphate, an aqueous solution of sodium silicate, and an aqueous solution of potassium silicate.

7. The gas sensor in accordance with claim 6, wherein the content of said auxiliary filler is in a range from 0.1 to 10 wt. % relative to 100 wt. % of said at least one of said plurality of powder filler layers.

8. The gas sensor in accordance with claim 6, wherein a powder filler layer disposed closest to the distal end side of said sealing member contains said auxiliary filler.

9. The gas sensor in accordance with claim 8, wherein said sealing member includes another powder filler layer containing no auxiliary filler.

10. The gas sensor in accordance with claim 5, wherein said auxiliary filler contains at least one component selected from the group consisting of barium hydroxide, borosilicate glass, alumino-silicate glass, soda-lime silicate glass, lead silicate glass, low-melting borate glass, lime alumino-based glass, and aluminate glass.

11. The gas sensor in accordance with claim 10, wherein the content of said auxiliary filler is in a range from 0.5 to 30 wt. % relative to 100 wt. % of said at least one of said plurality of powder filler layers.

12. The gas sensor in accordance with claim 1, wherein said powder filler layers contain either talc or boron nitride by an amount equal to or greater than 50 wt % relative to 100 wt. % of said powder filler layers.

13. A gas sensor comprising:
an element assembly inserted in a cylindrical housing, said element assembly including a sensor element and a cylindrical insulating tube assembled around said sensor element;
a measured gas cover provided at a distal end side of said housing to cover a distal end side of said sensor element; and
an atmospheric air cover provided at a proximal end side of said housing to cover a proximal end side of said sensor element,
wherein a clearance between an inside surface of said housing and an outside surface of said element assembly is gastightly sealed with a sealing member including a plurality of powder filler layers made of the same material as one another, and
wherein the powder filler layers directly contact with each other.

14. The gas sensor in accordance with claim 13, wherein said plurality of powder filler layers include predetermined powder material containing particles whose particle sizes are in a range from 80 to 1000 μm by an amount equal to or greater than 80 wt. % of the entire weight.

15. The gas sensor in accordance with claim 13, wherein said plurality of powder filler layers include a first powder filler layer positioned closest to the distal end side of said gas sensor,
said first powder filler layer contacts with an inside inclined surface provided on an outside surface of said element assembly and inclined from said element assembly to said housing,
said first powder filler layer contacts with an outside inclined surface provided on an inside surface of said housing and inclined from said housing to said element assembly, and
conditions of $0° \leq C \leq 50°$, $0° \leq D \leq 50°$, and $120° \leq E \leq 180°$ are satisfied
where 'C' represents an angle formed between said inside inclined surface and a line normal to an axial direction of said gas sensor,
'D' represents an angle formed between said outside inclined surface and said line normal to the axial direction of said gas sensor, and
'E' represents an angle formed between said inside inclined surface and said outside inclined surface.

16. The gas sensor in accordance with claim 13, further comprising a packing member contacting with an end surface of at least one of said plurality powder filler layers.

17. The gas sensor in accordance with claim 13, wherein at least one of said plurality of powder filler layers contains an auxiliary filler.

18. The gas sensor in accordance with claim 17, wherein said auxiliary filler contains at least one component selected from the group consisting of barium hydroxide, borosilicate glass, alumino-silicate glass, soda-lime silicate glass, lead silicate glass, low-melting borate glass, lime alumino-based glass, and aluminate glass.

19. The gas sensor in accordance with claim 18, wherein the content of said auxiliary filler is in a range from 0.5 to 30 wt. % relative to 100 wt. % of said at least one of said plurality of powder filler layers.

20. The gas sensor in accordance with claim 17, wherein a powder filler layer disposed closest to the distal end side of said sealing member contains said auxiliary filler.

21. The gas sensor in accordance with claim 20, wherein said sealing member includes another powder filler layer containing no auxiliary filler.

22. The gas sensor in accordance with claim 17, wherein said auxiliary filler is selected from the group consisting of an aqueous solution of primary aluminum phosphate, an aqueous solution of sodium silicate, and an aqueous solution of potassium silicate.

23. The gas sensor in accordance with claim 22, wherein the content of said auxiliary filler is in a range from 0.1 to 10 wt. % relative to 100 wt. % of said at least one of said plurality of powder filler layers.

24. The gas sensor in accordance with claim 13, wherein said powder filler layers contain either talc or boron nitride by an amount equal to or greater than 50 wt. % relative to 100 wt. % of said powder filler layers.

25. A gas sensor comprising:
a cylindrical housing;
a sensor element inserted in said cylindrical housing;
a measured gas cover provided at a distal end side of said housing to shield a distal end side of said sensor element from measured gas; and
an atmospheric air cover provided at a proximal end side of said housing to shield a proximal end side of said sensor element from atmospheric air,
wherein a clearance between an inside surface of said housing and an outside surface of said sensor element is gastightly sealed with a sealing member including a first powder filler layer disposed closest to the proximal end side, a second powder filler layer disposed closest to the distal end side and a third powder filler layer disposed between the first and second powder filler layers so as to contact with each other, and
wherein the first and second powder filler layers are made of the same material as each other, while the third powder filler is made of a material different from those of the first and second powder filler layers.

26. The gas sensor in accordance with claim 25, wherein the second powder filler layer contains an auxiliary filler, and at least one of the first and third powder filler layers contains no auxiliary filler.

27. A gas sensor comprising:
an element assembly inserted in a cylindrical housing, said element assembly including a sensor element and a cylindrical insulating tube assembled around said sensor element;

a measured gas cover provided at a distal end side of said housing to cover a distal end side of said sensor element; and an atmospheric air cover provided at a proximal end side of said housing to cover a proximal end side of said sensor element, wherein a clearance between an inside surface of said housing and an outside surface of said element assembly is gastightly sealed with a sealing member including a plurality of powder filler layers, wherein at least one of said plurality of powder filler layers contains an auxiliary filler, wherein a powder filler layer disposed closest to the distal end side of said sealing member contains said auxiliary filler, and wherein said sealing member includes another powder filler layer containing no auxiliary filler.

* * * * *